United States Patent
Imran

(10) Patent No.: US 11,944,780 B2
(45) Date of Patent: *Apr. 2, 2024

(54) MULTI-STAGE BIODEGRADABLE DRUG DELIVERY PLATFORM

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 258 days.

This patent is subject to a terminal disclaimer.

(21) Appl. No.: 16/663,173

(22) Filed: Oct. 24, 2019

(65) Prior Publication Data
US 2020/0054828 A1  Feb. 20, 2020

Related U.S. Application Data

(63) Continuation of application No. 16/163,430, filed on Oct. 17, 2018, now Pat. No. 10,507,282, which is a continuation of application No. 14/218,429, filed on Mar. 18, 2014, now Pat. No. 10,130,760.

(60) Provisional application No. 61/799,194, filed on Mar. 15, 2013.

(51) Int. Cl.
| | |
|---|---|
| *A61D 7/00* | (2006.01) |
| *A61D 1/02* | (2006.01) |
| *A61K 9/00* | (2006.01) |
| *A61M 5/158* | (2006.01) |
| *A61K 39/00* | (2006.01) |

(52) U.S. Cl.
CPC ............ *A61M 5/158* (2013.01); *A61D 1/025* (2013.01); *A61D 7/00* (2013.01); *A61K 9/0024* (2013.01); *A61K 39/00* (2013.01); *A61M 2202/064* (2013.01); *A61M 2202/30* (2013.01); *Y02A 50/30* (2018.01)

(58) Field of Classification Search
CPC ....... A61K 39/00; A61K 9/0024; A61P 37/04; A61P 31/12; A61P 31/04
See application file for complete search history.

(56) References Cited

U.S. PATENT DOCUMENTS

| | | | |
|---|---|---|---|
| 3,629,413 | A | 12/1971 | Shechmeister et al. |
| 5,429,822 | A | 7/1995 | Gresser et al. |
| 5,593,697 | A | 1/1997 | Barr et al. |
| 5,916,584 | A | 6/1999 | O'Donoghue et al. |
| 5,980,508 | A | 11/1999 | Cardamone et al. |
| 7,473,247 | B2 | 1/2009 | Mikszta et al. |
| 8,353,863 | B2 | 1/2013 | Imran |
| 10,071,199 | B2 | 9/2018 | Imran |
| 10,130,760 | B2 | 11/2018 | Imran |
| 10,507,282 | B2 | 12/2019 | Imran |
| 2002/0004060 | A1* | 1/2002 | Heublein ........... A61B 17/1204 424/422 |
| 2002/0072735 | A1* | 6/2002 | Kupperblatt ......... A61K 9/4808 604/892.1 |
| 2003/0232082 | A1* | 12/2003 | Li ..................... A61K 9/2031 424/473 |
| 2003/0232083 | A1 | 12/2003 | Wynn et al. |
| 2005/0202072 | A1 | 9/2005 | Buch-Rasmussen et al. |
| 2007/0003596 | A1 | 1/2007 | Tittelbach et al. |
| 2007/0135908 | A1 | 6/2007 | Zhao |
| 2009/0187167 | A1 | 7/2009 | Sexton et al. |
| 2010/0080839 | A1* | 4/2010 | Van De Wijdeven ....... A61K 9/1652 424/426 |
| 2010/0204678 | A1 | 8/2010 | Imran |
| 2010/0233254 | A1 | 9/2010 | Miller |
| 2012/0010590 | A1 | 1/2012 | Imran |
| 2012/0130339 | A1 | 5/2012 | Farra |
| 2012/0277323 | A1 | 11/2012 | Kumar et al. |

FOREIGN PATENT DOCUMENTS

| | | |
|---|---|---|
| EP | 2355887 B1 | 8/2017 |
| IN | 6036CHENP2015 A | 7/2016 |
| JP | 2005528383 A | 9/2005 |
| JP | 2016513715 A | 5/2016 |
| WO | 03059329 A2 | 7/2003 |
| WO | 2014146077 A1 | 9/2014 |

OTHER PUBLICATIONS

IPC, "Recommended and Minimum Ages and Intervals Between Doses", Adapted from Table 1, ACIP General Recommendations on Immunization, Feb. 2012, obtained online on Oct. 22, 2021 from URL: https://dph.georgia.gov/sites/dph.georgia.gov/files/Immunizations/IPC-Recommended_and_Minimum-Intervals.pdf (Year: 2012).*
Marcotte et al., "Delayed Release of Water-soluble Macromolecules from Polylactide Pellets", Journal of Controlled Release, vol. 9, No. 1, Jun. 1, 1989, pp. 75-85.
Mark et al., "Subcutaneous Versus Intramuscular Injection for Booster DT Vaccination of Adolescents", Vaccine, vol. 17, No. 15-16, Apr. 9, 1999, pp. 2067-2072.
Willis, "Getting Unexpected Flyers? (Checkthe shape of your bullets)", Innovative Technologies, Available online at: http://www.larrywillis.com/bullet-shape.html, Apr. 5, 2012, 3 pages.

(Continued)

*Primary Examiner* — Robert T. Crow
*Assistant Examiner* — John P Nguyen
(74) *Attorney, Agent, or Firm* — Brooks Kushman P.C.

(57) ABSTRACT

Embodiments of the invention provide multi-stage biodegradable drug delivery platforms and methods for the subcutaneous delivery of therapeutic agents (TA). Embodiments of the platform may be configured to subcutaneously deliver a first dose of a first TA which is absorbed into the body and/or blood stream (BBS) to produce a first therapeutic effect for a first selectable time period (STP), and subsequently after a second STP, deliver a second dose of a second TA which is absorbed into the BBS to produce a second therapeutic effect for a third STP. An embodiment of the platform may comprise a body having a tissue-penetrating end, a primary cavity having a first TA dose and a shell having a secondary cavity having a second TA dose. The first TA dose is released after the first STP and the second TA dose is released after the second STP by biodegradation of the shell.

18 Claims, 3 Drawing Sheets

(56) References Cited

OTHER PUBLICATIONS

Wise et al., "Opportunities and Challengesin the Design of Implantable Biodegradable Polymeric Systems forthe Delivery of Antimicrobial Agents and Vaccines", Advanced Drug Delivery Reviews, vol. 1, No. 1, May 1, 1987, pp. 19-39.

\* cited by examiner

MULTI-STAGE BIODEGRADABLE DRUG DELIVERY PLATFORM

CROSS-REFERENCES TO RELATED APPLICATIONS

This application is a continuation of U.S. patent application Ser. No. 16/163,430, filed on Oct. 17, 2018, which is a continuation of U.S. patent application Ser. No. 14/218,429, filed on Mar. 18, 2014, now U.S. Pat. No. 10,130,760, which claims priority to U.S. Provisional Patent Application No. 61/799,194, filed on Mar. 15, 2013, which is hereby incorporated by reference herein for all purposes. This application is further related to the following U.S. patent application Ser. No. 14/218,409, now U.S. Pat. No. 10,071,199 also titled "Multi-Stage Biodegradable Drug Delivery Platform," filed Mar. 18, 2014, and is hereby incorporated by reference herein for all purposes.

FIELD OF THE INVENTION

Embodiments of the invention described herein relate to drug delivery. More specifically embodiments relate to subcutaneous drug delivery. Still more specifically, embodiments relate to a device and method for the subcutaneous delivery of drugs, vaccines and other therapeutic agents in more than one stage over extended periods of time.

BACKGROUND

Both oral and intravenous forms of drug delivery have a number of limitations. Oral delivery limitations include toxicity, poor absorption and varying concentrations over time. Intravenous limitations include the requirement to mix and store the drug in liquid form as well as the use of sterile technique. These can be particularly problematic in rural areas where adequate refrigeration and sterile needles are not necessarily readily available, limiting shelf life and exposing the patient to infection. Thus, there is a need for improved methods of drug delivery which can extend shelf life and are more easily used in settings lacking refrigeration or sterile medical supplies.

An additional challenge in drug delivery is administrating a medication regimen which requires an initial delivery of a medication (e.g. drugs, vaccines and other therapeutic agents) followed by one or more subsequent "booster shot" dosages of medication, significantly later in time, in order to complete the medication regimen. Such a regimen adds time and costs to all concerned as well the risk that the subsequent dose is administered late or missed altogether. Administration of such a medication regimen can be particularly problematic in rural areas where there is logistical difficulty in finding and/or treating a patient with one or more subsequent dosages.

Some of the same challenges also present themselves in inoculating livestock with a medication that requires one or more booster shots. Administering a dosage of medication requires herding the livestock followed by the isolating and pacifying of each individual animal in order to deliver the medication dosage. Administering a booster shot dosage in the same manner to the same livestock requires the effort and cost of herding the livestock and the isolating and pacifying of each individual animal one or more subsequent times. This challenge can also be seen in providing medication to humans, where the patient may be unable to return to a doctor to receive a second, third, and/or subsequent booster shot as part of a medication regimen.

Thus, there is a need for improved methods of medication delivery which can deliver subsequent dosages of a medication regimen without the need for the patient (which can include a human or other animal such as bovine livestock) to return to the administrator of the initial medication, or for the administrator of the initial medication to actively seek out and find the patient.

SUMMARY OF THE INVENTION

Various embodiments of the invention described herein provide a multi-stage biodegradable drug delivery device, apparatus, and methods for the subcutaneous delivery of drugs, vaccines and other therapeutic agents. Many embodiments provide a multi-stage biodegradable drug delivery device that can penetrate the skin of a patient (either a human or other mammal) and subcutaneously deliver a first selectable dose of a first therapeutic agent which can be absorbed into the body tissue and/or blood stream to produce a first therapeutic effect for a first selectable period of time, and subsequently after a second selectable period of time, deliver a second selectable dose of a second therapeutic agent which can be absorbed into the body tissue and/or blood stream to produce a second therapeutic effect for a third selectable period of time. In various embodiments, the drug and/or other therapeutic agents can be in the form of a liquid, a gel, a colloid, and/or in solid form as a slug, pellet, powder, or another solid structure.

Further embodiments described herein provide a multi-stage biodegradable drug delivery device that can penetrate the skin of a patient and subcutaneously deliver a first selectable dose of a first therapeutic agent which can be absorbed into the body tissue and/or blood stream to produce a first therapeutic effect for a first selectable period of time, subsequently, after a second selectable period of time, deliver a second selectable dose of a second therapeutic agent which can be absorbed into the body tissue and/or blood stream to produce a second therapeutic effect for a third selectable period of time, and subsequently, after a fourth selectable period of time, deliver a third selectable dose of a third therapeutic agent which can be absorbed into the body tissue and/or blood stream to produce a third therapeutic effect for a fifth selectable period of time.

One embodiment provides a multi-stage biodegradable drug delivery device for the subcutaneous delivery of therapeutic agents in solid or liquid form which includes a core body and a skin penetrating end, in which the core body is detachably coupled to a distal end of a delivery apparatus or structure, such as a shaft. In aspects, the multi-stage biodegradable drug delivery device can be a skin penetrating device that is fabricated from a solid composition that is configured to dissolve in body tissue fluids and be absorbed into the body tissue and/or blood stream. The penetrating end has an arrow head or other shape that is configured to penetrate and lodge beneath the skin of a patient when inserted through the skin by force applied from the shaft. This can be done by holding the delivery apparatus in the user's fingers and poking the skin or through means of a mechanism (such as a modified syringe plunger) which advances the delivery apparatus or the skin penetrating device itself into the skin. The penetrating end may also penetrate through and lodge within subcutaneous, dermal, and/or subdermal tissue. When the penetrating end and core body are advanced into the skin and the delivery apparatus is pulled away from the skin, the core body detaches from the delivery apparatus and is retained beneath the skin typically, in a muscular layer.

Embodiments of the invention are particularly useful for the delivery of vaccines and other medication requiring multiple doses that need to be delivered over staggered period of time such as days or even months.

Further details of these and other embodiments and aspects of the invention are described more fully below, with reference to the attached drawing figures.

DETAILED DESCRIPTION OF THE INVENTION

Certain embodiments of the present invention provide for a two-stage biodegradable drug delivery platform, wherein the platform is capable of penetrating the skin of, and being inserted subcutaneously within, a human patient or other mammal such as various livestock, including bovine livestock. Other embodiments of the present invention provide for a three-stage biodegradable drug delivery platform, wherein the platform is capable of penetrating the skin of a human patient or other mammal (e.g., bovine or other livestock), and being inserted subcutaneously within a human or other mammal.

Figure 1A:
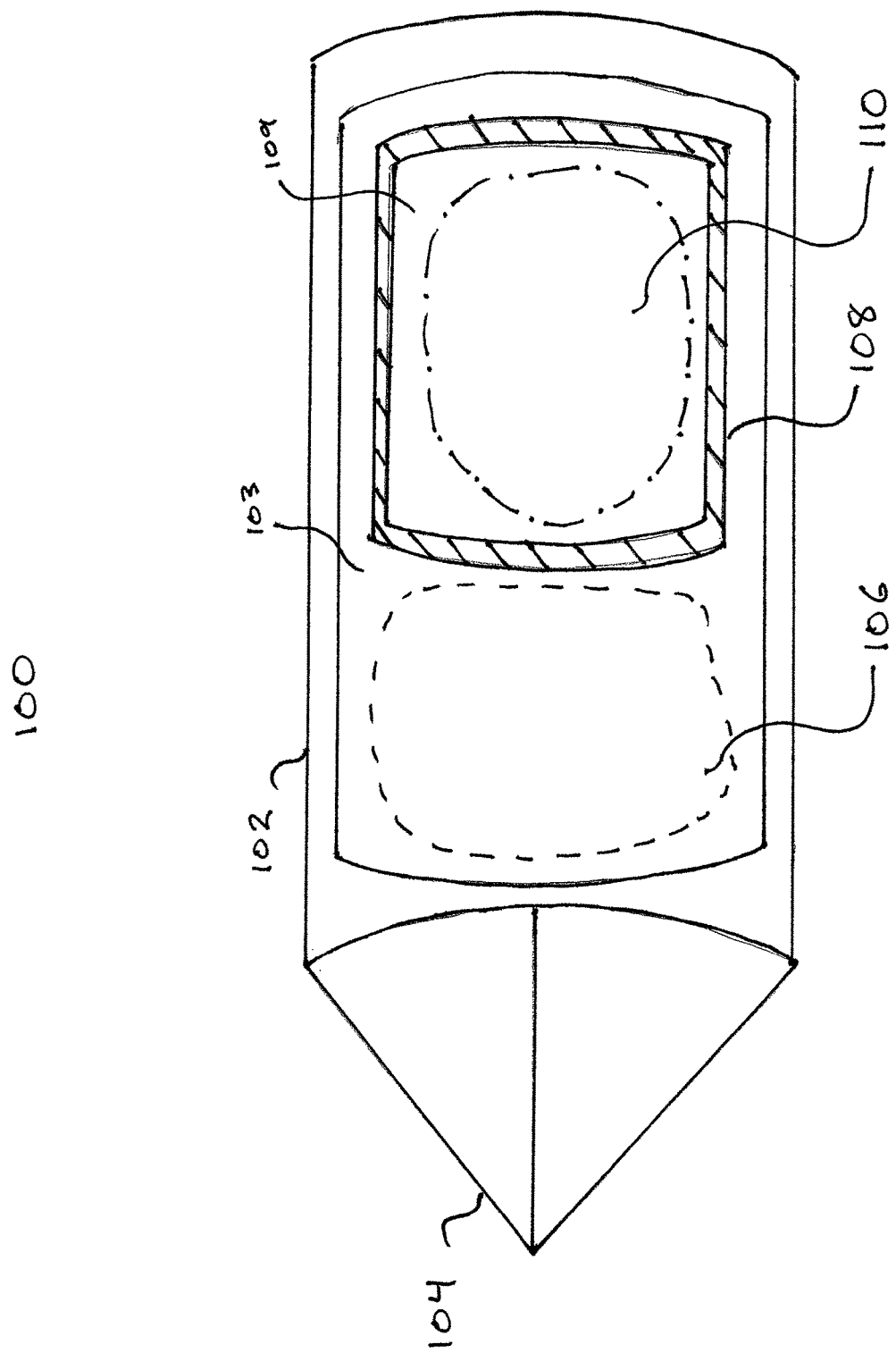
FIG. 1A depicts a cross-sectional schematic of a two-stage biodegradable drug delivery platform.

FIG. 1A depicts a cross-sectional schematic of an embodiment of a two-stage biodegradable drug delivery platform 100, which is shaped in the form of a needle and can include a core body 102 and a penetrating end 104. The core body 102 of the biodegradable drug delivery platform 100 can include a first biodegradable material, and may include one or more biodegradable polymers such as PLGA (poly(lactic-co-glycolic) acid), poly-lactic acid, cellulose, as well as sugars such as maltose or other biodegradable material described herein or known in the art. The penetrating end 104 can be fabricated from the same biodegradable material as the core body 102. The core body 102 is at least in-part hollow, with a primary cavity 103. The penetrating end 104 may be beveled or tapered to a point to allow for the puncture of a skin surface. Related surface penetrating structures, delivery methods, and therapies which may be adapted for use in embodiments of the present invention may be more fully understood with reference to U.S. Pat. No. 8,353,863, which issued from U.S. patent application Ser. No. 12/705,529, the full disclosure of which is incorporated herein by reference.

The primary cavity 103 can contain a first dosage of a therapeutic agent 106 (e.g., an initial dose of vaccine, birth control drug, etc.), which can be in the form of a liquid, a gel, a colloid, or in solid form as a slug, pellet, powder, or another solid structure. The primary cavity 103 can also contain a secondary shell 108, which is also at least in-part hollow, having a secondary cavity 109. The secondary shell 108 can either include or be composed of a second biodegradable material, such as magnesium (Mg) that is different than the first biodegradable material. The magnesium used can comprise pure magnesium or various alloys thereof which are known in the biomaterials arts to degrade in the body. Suitable magnesium alloys may include for example, alloys containing one more of zinc (Zn), manganese (Mn), aluminum (Al), calcium (Ca), lithium (Li), zirconium (Zr), yttrium (Y), and rare earth metals. The secondary cavity 109 can contain a second dosage of a therapeutic agent 110 (e.g., a booster dose of vaccine, secondary dose of birth control drug, etc.), which can be in the form of a liquid, a gel, a colloid, or in solid form as a slug, pellet, powder, or another solid structure. The first dosage of a therapeutic agent 106 and the second dosage of a therapeutic agent 110 can be the same therapeutic agent at the same dosage and/or concentration, the same therapeutic agent at different dosages and/or concentrations, or different therapeutic agents at similar or dissimilar dosages. In other embodiments, the first dosage of a therapeutic agent 106 and the second dosage of a therapeutic agent 110 can comprise one or more of the same therapeutic agents. In many embodiments of the invention, delivery of a therapeutic agent from a multi-stage biodegradable drug delivery platform does not require that a biomaterial completely biodegrade, but rather that a sufficient proportion of a biomaterial degrades such that a therapeutic agent can egress from a cavity (e.g. through an aperture, diffusing through the biomaterial, etc.) which is defined by a structure comprised of the biomaterial.

According to one embodiment, the core body 102 can be fabricated from a first biodegradable material configured to quickly biodegrade in vivo, typically within about twenty (20) minutes, after subcutaneous insertion of the two-stage biodegradable drug delivery platform 100 into the body of a patient. According to other embodiments, the first biodegradable material can be fabricated from materials configured to biodegrade in vivo, over various periods of time, for example one (1) hour, two (2) hours, four (4) hours, six (hours), twelve (12) hours, or over periods of time in between or beyond the embodiments listed. Upon biodegradation of the core body 102, the first dosage of a therapeutic agent 106 is released into the body of the patient; this release of the first dosage 106 comprises the first stage of drug delivery from the two-stage biodegradable drug delivery platform 100. Additionally, upon biodegradation of the core body 102, the secondary shell 108 is directly exposed to the in vivo conditions of the patient's body. The secondary shell 108 biodegrades at a slower rate than the core body 102. Accordingly, the thicker the secondary shell 108 walls are, the proportionally more time it takes for the secondary shell to completely biodegrade. Upon biodegradation of the secondary shell 108, the second dosage of a therapeutic agent 110 is released into the body of the patient; this release of the second dosage 110 is the second stage of drug delivery from the two-stage biodegradable drug delivery platform 100. In various aspects, both or each of the first dosage and second dosage can have different amounts of mass of one or more therapeutic agent.

Various factors can be taken into consideration in the selection of the wall thickness and other dimension of the secondary shell 108. These can include one more of the volume of the primary cavity, the desired degradation of the shell including the degradation for release of second 106 or third dose 110 of medication and the intended implant site for platform 100. In various embodiments of the two-stage biodegradable drug delivery platform 100, the size and volume of the secondary shell 108 can be limited by the size and volume of the primary cavity 103, and accordingly, while the walls of the secondary shell 108 may be of varying thicknesses, the wall thicknesses are also limited by the size and volume of the primary cavity 103. In some embodiments, the walls of the secondary shell 108 can be about one (1) thousandth of an inch thick, about five (5) thousandths of an inch thick, about ten (10) thousandths of an inch thick, about twenty (20) thousandths of an inch thick, or any range of thicknesses between and including these thicknesses. According to one more embodiments, the walls of the secondary shell 108 can be configured to have a thickness such that the secondary shell 108 retains its structural integrity and does not biodegrade for a selected period of time. In particular, the secondary shell 108 can have walls that are thick enough to remain intact in vivo for about three months, about six months, about nine months, or for any period of time including and in between these durations. Wall thickness for longer periods of time are also contemplated, such as thicknesses to achieve one year, two year, five years and even longer periods. Thus, in aspects, a first time period for biodegradation of the first biodegradable material can be substantially shorter than a second time period for biodegradation of the second biodegradable material. The appropriate wall thickness can be determined based on mass transfer and/or kinetic relationships known in the art including for example Fickian and non-Fickian diffusion, electrochemical rate equations, zero, first order and second order kinetic equations, and Arrhenius equations. In some aspects, the first biodegradable material can biodegrade at a faster rate than the second biodegradable material, based upon the thickness of the materials or physical characteristics of the materials.

Figure 1B:
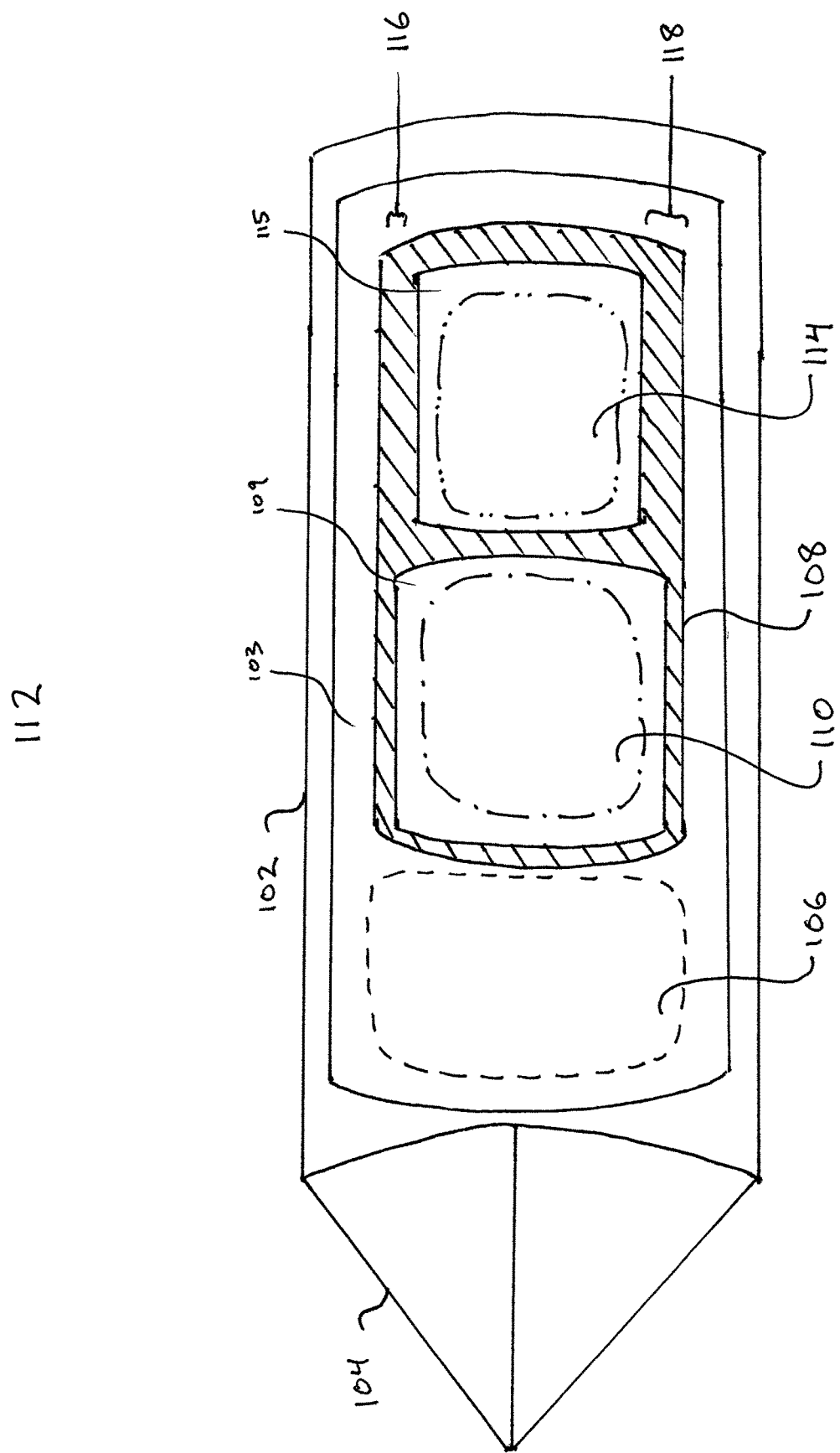
FIG. 1B depicts a cross-sectional schematic of a three-stage biodegradable drug delivery platform.

FIG. 1B depicts a cross-sectional schematic of an embodiment of a three-stage biodegradable drug delivery platform 112. According to this embodiment, the platform can be in the form of a needle or like shape and includes a core body 102 and a tissue penetrating end 104. The core body 102 is at least in-part hollow and has a primary cavity 103. As in the two-stage biodegradable drug delivery platform 100, in embodiments of a three-stage biodegradable drug delivery platform 112 the core body 102 as well as the tissue penetrating end 104 can be made of the same material, such as a first biodegradable material as described above (though in some embodiments penetrating end 104 can be made of a material that has in increased hardness for better tissue penetrating ability). Penetrating end 104 can beveled or tapered (or have other tissue penetrating shape) to allow for puncture of the skin of an animal. The core body 102 is again at least in-part hollow, with a primary cavity 103.

The primary cavity 103 in the three-stage biodegradable drug delivery platform 112 also contains a first dosage of a therapeutic agent 106, which can be in the form of a liquid, a gel, a colloid, or in solid form as a slug, pellet, powder, or another solid structure. The primary cavity 103 can also contain a secondary shell 108, which is also at least in-part hollow, and can include divided and separate compartments which may include at least a secondary cavity 109 and a tertiary cavity 115. The secondary shell 108 can be made of a second biodegradable material, as described above, which is different than the first biodegradable material so that the secondary shell biodegrades at different rate then the core body. The secondary cavity 109 can contain a second dosage of a therapeutic agent 110, which can be in the form of a liquid, a gel, a colloid, or in solid form as a slug, pellet, powder, or another solid structure. The tertiary cavity 115 can contain a third dosage of a therapeutic agent 114, which can be in the form of a liquid, a gel, a colloid, or in solid form as a slug, pellet, powder, or another solid structure. The first dosage of a therapeutic agent 106, the second dosage of a therapeutic agent 110, and the third dosage of a therapeutic agent 114 can be the same therapeutic agent at the same dosage and/or concentration, the same therapeutic agent at different dosages and/or concentrations, or different therapeutic agents at similar or dissimilar dosages. Further, in some embodiments, two of the three dosages may be identical, while the third of the three dosages is different. In various aspects, any or each of the first dosage, second dosage, and third dosage can have different amounts of mass of one or more therapeutic agent.

In various embodiments, the walls of the secondary shell 108 can be of varying thicknesses, depending on the amount of time the secondary shell is desired to remain intact. Generally, the thicker the secondary shell 108 wall, the more time it takes before the secondary shell completely biodegrades. Thus, according to one more embodiments, thicker walls for secondary shell 108 can be used when longer degradation times of the shell are desired. Also, according to one or more embodiments, the thickness of the secondary shell 108 wall defining the secondary cavity 109 (encapsulating the second dosage 110) can be thinner than the thickness of the secondary shell 108 wall defining the tertiary cavity 115 (encapsulating the third dosage 114). Specifically, the secondary shell 108 of the three-stage biodegradable drug delivery platform 112 can have a first wall thickness 116 which surrounds and defines the secondary cavity 109, in which the second dosage 110 is encapsulated. Similarly, the secondary shell 108 of the three-stage biodegradable drug delivery platform 112 can have a second wall thickness 118 which surrounds and defines the tertiary cavity 115, in which the third dosage 114 is encapsulated.

In various embodiments of the invention, the release of therapeutic agent (including the period when it is released after implant of platform 100) from the secondary and tertiary cavities 109 and 115 can be controlled by the wall thicknesses of shell 108 including for example thicknesses 116 and 118 as well as the material(s) selected for shell 108. Accordingly in some embodiments, the first wall thickness 116 is thinner than the second wall thickness 118 so as to have secondary cavity 109 release its therapeutic agent sooner than tertiary cavity 115. This is due to the fact that secondary shell 108, comprised of the second biodegradable material, biodegrades at a steady rate in vivo, thus the portion of the secondary shell 108 bounded only by the first wall thickness 116 does not remain intact in vivo for as long of a period of time as the portion of the secondary shell 108 bounded by the second wall thickness 118. Thus the shell around secondary cavity 109 breaks down sooner than that surrounding tertiary cavity 115. In alternative or additional embodiments, the release of therapeutic agents can also be controlled by selection of the materials for shell 108. For example, the material of shell 108 surrounding secondary cavity 109 can be configured to biodegrade at a faster rate than tertiary cavity 115, so at have second therapeutic agent dose 110 release sooner than third therapeutic agent dose. As described above, the rates of degradation of the shell 108 can also be controlled by the selection of the material for the shell. For magnesium and other metals this can include the use one more of various alloys (which can slow rates of degradation), impurities, heat treatment (e.g. annealing, solution, and age treatments and the like as are known in the art) and coatings.

According to one embodiment of the invention, the core body 102 can be comprised of a first biodegradable material that is configured to quickly biodegrade in vivo, typically within twenty (20) minutes, after subcutaneous insertion of the three-stage biodegradable drug delivery platform 112 into the body of a patient. In alternative embodiments, the first biodegradable material can be configured to biodegrade in vivo, over various periods of time, for example within one (1) hour, two (2) hours, four (4) hours, six (hours), twelve (12) hours, or over periods of time in between or beyond the embodiments listed.

A discussion will now be presented of the different stages of drug delivery obtainable by one or more embodiments of delivery platform 100. Upon biodegradation of the core body 102, the first dosage of a therapeutic agent 106 is released into the body of the patient; this release of the first dosage 106 (e.g., a first dose of vaccine, antibiotic, birth control agent, etc.) constitutes the first stage of drug delivery from the three-stage biodegradable drug delivery platform 112. Upon biodegradation of the core body 102, the secondary shell 108 is configured to be directly exposed to the in vivo conditions of the patient's body (e.g., exposure to fluids in sub-dermal or other tissue) and thus begin to biodegrade. Accordingly, the portion of the secondary shell 108 bounded only by the first wall thickness 116 degrades after a first selected period of time, exposing the secondary cavity 109 to the in vivo environment, releasing the second dosage of a therapeutic agent 110 (e.g., a booster dose of vaccine, or second dose of antibiotic, birth control agent, etc.) over a second selected period of time. The release of the second dosage 110 constitutes the second stage of drug delivery from the three-stage biodegradable drug delivery platform 112. Subsequently, the portion of the secondary shell 108 bounded by the second wall thickness 118 degrades after a third selected period of time, exposing the tertiary cavity 115 to the in vivo environment, releasing the third dosage of a therapeutic agent 110 over a fourth selected period of time; this release of the second dosage 110 constitutes the third stage of drug delivery from the three-stage biodegradable drug delivery platform 112.

In various embodiments of the three-stage biodegradable drug delivery platform 122, the first wall thickness 116 of the secondary shell 108 can be about one (1) thousandth of an inch thick, about five (5) thousandths of an inch thick, about ten (10) thousandths of an inch thick, or any range of thicknesses between and including these thicknesses. Further, the second wall thickness 118 of the secondary shell 108 can be about five (5) thousandths of an inch thick, about ten (10) thousandths of an inch thick, about twenty (20) thousandths of an inch thick or any range of thicknesses between and including these thicknesses. The second wall thickness 118 of the secondary shell 108 is generally thicker than the first wall thickness 116, such that as the second biodegradable material biodegrades in vivo, the secondary cavity 109 is exposed, and the second dosage 110 delivered, to the in vivo environment before the tertiary cavity 115 is exposed, and the third dosage 114 delivered, to the in vivo environment. In particular, the first wall thickness 116 of the secondary shell 108 may be thick enough to remain intact in vivo (maintaining the structural integrity of the secondary cavity 109) for about three months, about six months, or about nine months, or for any period of time including and in between these durations, while the second wall thickness 118 is thick enough to remain intact in vivo (maintaining the structural integrity of the tertiary cavity 115) for a relatively longer period of time.

In alternative embodiments of the invention, the secondary shell 108 can have a plurality of cavities, that allow for a fourth, fifth, or even greater number of dosages to be delivered by a multi-stage drug delivery platform. Further, in other alternative embodiments of the invention, wall thicknesses that provide for longer periods of time before biodegrading are also contemplated, including, but not limited to, thicknesses of fifty (50), one hundred (100), one hundred fifty (150), or two hundred (200) thousandths of an inch, and thickness ranges in between.

In various embodiments, the weight of the core body 102 and penetrating end 104 can range between about 150 mg to about 400 mg, with larger and smaller weights contemplated. For embodiments of the core body 102 and tissue penetrating end 104 fabricated from maltose, the weight can range from about 190 mg to about 380 mg. In various embodiments, the weight of the secondary shell 108 can range from about 90 mg to about 150 mg, with larger and smaller weights contemplated. For embodiments of the secondary shell 108 fabricated from magnesium, the weight can range from about 93 mg to about 141 mg. Even larger and smaller weights are contemplated. A particular weight of a core body and corresponding dosage of therapeutic agent can be selected depending on one or more of the size and age of the patient.

In alternative embodiments of the invention, an additional drug, vaccine or other therapeutic agent, which can be the same or different drug or therapeutic agent as the first dosage 106, the second dosage 110, and/or the third dosage 114, can be mixed in with the biodegradable material that forms the core body 102 and/or penetrating end 104 of the biodegradable drug delivery platform 100. In such embodiments, the penetrating end 104 can comprise a substantially heterogeneous mixture of a drug and the biodegradable material used to form the overall biodegradable drug delivery platform 100.

Figure 2:
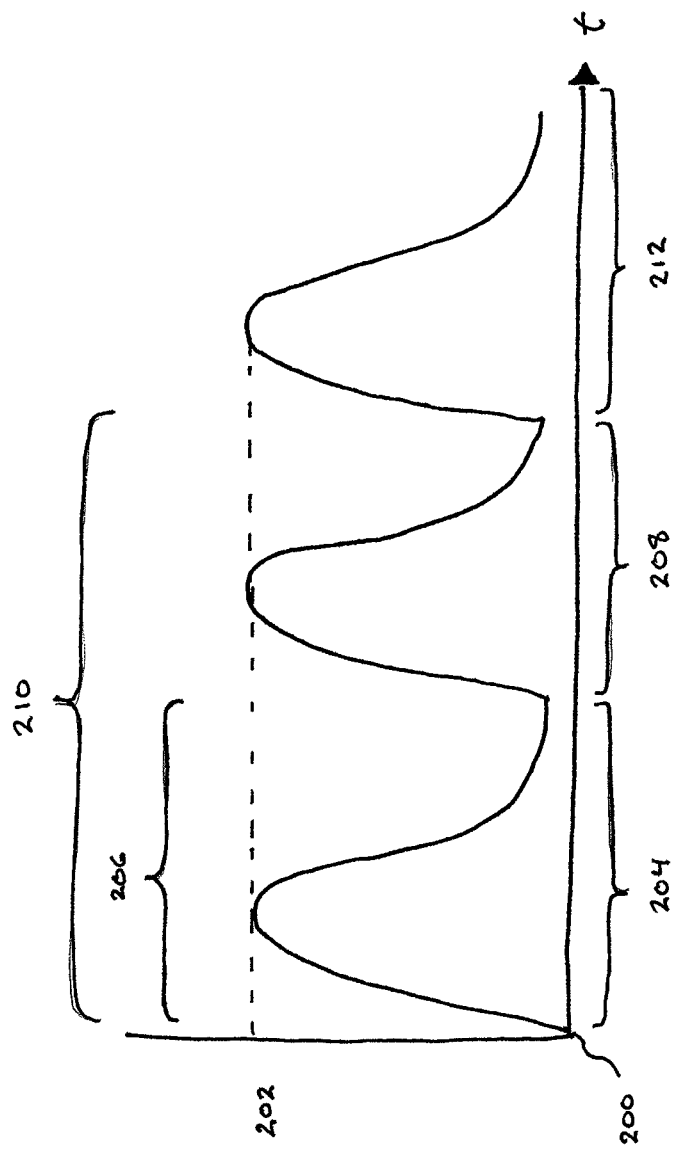
FIG. 2 is an illustration modeling the delivery of a drug from a three-stage biodegradable drug delivery platform.

FIG. 2 is an illustration modeling the delivery of one or more drugs over time from an embodiment of a three-stage biodegradable drug delivery platform 112. At the time of injection 200 of the three-stage biodegradable drug delivery platform 112, the first biodegradable material begins to biodegrade and soon thereafter delivers a dosage 202 of the first therapeutic agent over a first selectable period of time 204. The portion of the secondary shell 108 defining the secondary cavity 109 is configured to biodegrade after a second selectable period of time 206, after which a dosage 202 of the second therapeutic agent is delivered for a third selectable period of time 208. The portion of the secondary shell 108 defining the tertiary cavity 115 is configured to biodegrade after a fourth selectable period of time 210, after which a dosage 202 of the third therapeutic agent is delivered for a fifth selectable period of time 212. In various embodiments of the invention, the dosage 202 of the various therapeutic agents can be of the same or different volumes, and can be of the same or different therapeutic agents, at similar or dissimilar concentrations. Further, the selectable periods of time that the therapeutic agents can be delivered can be of the same or different durations of time.

Many embodiments of the invention provide for the delivery of a drug or other therapeutic agent in a bolus dose. In particular embodiments, either one or both of delivery of the first dosage of therapeutic agent and the delivery of the last dosage of a therapeutic agent can be delivered as a bolus. At the time of injection, the first therapeutic agent can be delivered as a bolus, releasing a dosage of the first therapeutic agent within a human, a mammal, or other animals soon thereafter. In embodiments of the invention, there may be a quiescent period of time after delivery of the first therapeutic agent and before delivery of the second therapeutic agent where there is no therapeutic agent being delivered from the multi-stage biodegradable drug delivery platform to the body of the human or other animal that has been injected. A quiescent period can be a period of days, weeks, months, or years. In embodiments of the invention where more than one dosage of therapeutic agents is delivered to the body of a human or other animal, one or more of the deliveries of a dosage of therapeutic agent may be followed by a quiescent period where no therapeutic agent is delivered from the multi-stage biodegradable drug delivery platform. The delivery of a therapeutic agent as a bolus can be employed in combination with a relatively gradual delivery of a therapeutic agent. For example, in some embodiments, a dosage of a first therapeutic agent may be released as a bolus over a first selectable period of time, after which for a second selectable period of time which is quiescent and no therapeutic agent is delivered, a dosage of a second therapeutic agent is released over a third selectable period of time which is relatively longer than the first selectable period of time. Subsequently, after a fourth selectable period of time, a dosage of a third therapeutic agent can be delivered as a bolus to the human or other animal for a fifth selectable period of time which can be similar in duration to the first selectable period of time. In embodiments of the invention, every dosage of therapeutic agents delivered may be delivered as a bolus.

Vaccine Embodiments. Many embodiments can be configured for the delivery of vaccine in humans and other animals where the vaccine regimen requires an initial dose followed by a booster dose. A booster dose is an extra administration of a vaccine after an earlier dose. After initial immunization, a booster injection or booster dose is a re-exposure to the immunizing antigen in the initial dose. The booster dose can be given to increase immunity against that antigen back to protective levels after it has been shown to have decreased or after a specified period.

Humans Vaccines Having Booster Doses. Some of the vaccines delivered to humans which may require booster doses which can be delivered by one or more embodiments of the invention can include but are not limited to the following: hepatitis A, hepatitis B, hepatitis C, tetanus, Tetanus, diphtheria, pertussis (given all at once known as Td/Tdap) measles, Human papillomavirus (HPV), Varicella (chickenpox) and meningococcal vaccine, polio virus vaccine (inactivated, Rotar virus vaccine, Haemophilus influenzae type vaccine and pneumococcal conjugate vaccine. Still other vaccines are contemplated including all of the multi-dose vaccines (not included on this list), which are given in a typical vaccine schedule for infants, toddlers, children, teenagers and adults. In various embodiments, the booster doses of a specific vaccine can be configured to be delivered in one or more secondary shells 108 described herein which are configured to degrade in a selected time period (e.g., 3 months, 6 months, etc.) to deliver the first and/or subsequent booster doses of the vaccine. According to various embodiments, shell 108 can be fabricated from one or more of magnesium, magnesium alloys, or other biodegradable material known in the art. The particular dimensions (e.g., thickness, etc.) and other properties of the magnesium or other shell 108 (e.g. composition (corrosion resistance, biodegradation rate, density, composition (alloys and impurities etc.) can be adapted for the particular size, and age of the patient (infant, toddler, teenager or adult) so as to achieve the desired release period of the first or any other subsequent booster dose. The amount and composition of the booster itself can also be factored into the dimensions of the shell. For example, increased wall thickness may be used for vaccines which themselves can have biodegradative effect on the shell or accelerate the biodegradation of the shell.

Vaccines for Bovines Having Booster Doses. Some of the vaccines for various bovine infectious diseases delivered to bovine and other livestock which may require booster doses which can be delivered by one or more embodiments of the invention are listed in the tables below by category of animal along with schedule for initial dose and subsequent booster doses. Still other vaccines are contemplated. Again in various embodiments, the booster doses of the of the specific vaccine be configured to be delivered in one or more secondary shells 108 described herein, which may comprise magnesium or other biodegradable material, which is configured to degrade in a selected time period after to deliver the first and/or subsequent booster doses of the vaccine. The particular dimensions (e.g., thickness, etc.) and other properties of the magnesium or other shell 108 can be adapted for the particular size, and age of the livestock so as to achieve the desired release period of the first or any other subsequent booster dose.

TABLE 1

Vaccine Schedule for Cows and Bulls

| Vaccine, | When |
| --- | --- |
| IBR | Annual (killed or intranasal) |
| BVD | Annual |
| PI3 | Annual |
| BRSV | Annual |
| Leptospirosis (5-Way) | Annual (every 3 to 6 months in some areas) |
| Vibriosis | Annual (30 to 60 days before breeding) |
| Trichomoniasis | Annual (30 to 60 days before breeding) |
| Pinkeye | As needed |
| Blackleg 7-Way | Annual |
| Anthrax | As directed |

TABLE 2

Vaccine Schedule for Calves

| Vaccine, | When |
| --- | --- |
| Blackleg 7-Way | Preweaning |
| IBR-BVD-PI3 | Preweaning |
| Leptospirosis | Preweaning |
| Brucellosis | Heifers (4 to 12 months) |
| BRSV | As needed |
| Pasteurella | Preweaning |
| Haemophilus somnus | Preweaning |
| Pinkeye | As needed |
| E. coli | Vaccinate cows (twice 30 days before calving) |
| Anthrax | As directed |
| Anaplasmosis | As directed |

TABLE 3

Vaccine Schedule for Heifers

| Vaccine, | When |
| --- | --- |
| Brucellosis | Calfhood (4 to 12 months) |
| IBR | Before breeding |
| BVD-PI3 | Before breeding |
| BRSV | Before breeding |
| Vibriosis | Before breeding |
| Leptospirosis | Before breeding |
| Blackleg 7-Way | Before breeding |
| Anthrax | Optional as directed |
| Anaplasmosis | Optional as directed |

Embodiments Of Methods For Multi Stage Drug Delivery. Various additional embodiments of multi state drug delivery using embodiments of the multistage drug delivery device will now be presented. In some embodiments of the invention, a method of delivering a drug in multiple stages may comprise: (1) implanting a multi-stage biodegradable drug delivery platform into a patient, where the multi-stage biodegradable drug delivery platform is at least in part fabricated from a first biodegradable material which biodegrades in vivo, (2) delivering a first therapeutic agent to the patient after the first biodegradable material of the multi-stage biodegradable drug delivery platform biodegrades, and (3) delivering a second therapeutic agent to the patient, after a second biodegradable material, which biodegrades in vivo at a slower rate than the first biodegradable material, after the first potion of the second biodegradable material of the multi-stage biodegradable drug delivery platform biodegrades.

In other embodiments, a method of delivering a drug in multiple stages may comprise (1) implanting a multi-stage biodegradable drug delivery platform into a patient, where the multi-stage biodegradable drug delivery platform in at least in part constructed from a first biodegradable material which biodegrades in vivo, (2) delivering a first therapeutic agent to the patient after the first biodegradable material of the multi-stage biodegradable drug delivery platform biodegrades, (3) delivering a second therapeutic agent to the patient, after a second biodegradable material, which biodegrades in vivo at a slower rate than the first biodegradable material, after the first potion of the second biodegradable material of the multi-stage biodegradable drug delivery platform biodegrades, and (4) delivering a third therapeutic agent to the patient after a second potion of the second biodegradable material biodegrades.

In still other embodiments, a method of delivering a multi-stage biodegradable drug may comprise: advancing a penetrating end of a body through skin of a patient so as to lodge the body subcutaneously within the patient, wherein a shell is disposed within the body; releasing a first therapeutic agent dose from the advanced body within the patient; and releasing a second therapeutic agent dose from the shell within the patient at a desired period of time after the release of the first therapeutic agent dose by biodegrading the shell within the body.

Conclusion. The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments can be sized or otherwise adapted for various pediatric applications as well as a number of veterinary applications (e.g. canine, feline, equine, bovine, porcine, etc.).

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Also, the invention contemplates embodiments in which an element(s) shown and described in an embodiment is excluded from that embodiment. Hence, the scope of the present invention is not limited to the specifics of the described embodiments, but is instead limited solely by the appended claims.

What is claimed is:

1. A method for drug delivery, the method comprising:
    lodging a drug delivery platform in a tissue layer beneath skin of a patient, the drug delivery platform containing at least a first dosage and a second dosage of therapeutic agent, the first dosage contained in a primary cavity of a first biodegradable structure, wherein the first biodegradable structure comprises a core body, the second dosage contained in a secondary cavity of a second biodegradable structure, the second biodegradable structure contained in the primary cavity of the first biodegradable structure, the second biodegradable structure having a material composition different from the first biodegradable structure, the second biodegradable structure comprising a shell having a shell wall with a thickness of about 1 to about 20 thousandths of an inch and a weight of about 90 mg to about 150 mg, the shell wall having a material composition selected to time a release of the second dosage to a specified time subsequent to a release of the first dosage;
    biodegrading the first biodegradable structure in vivo over a first period of time to release the first therapeutic agent dosage;
    releasing the first dosage of therapeutic agent into the tissue of the patient;
    biodegrading the second biodegradable structure in vivo over a second period of time; and
    releasing the second dosage of therapeutic agent into the tissue of the patient after release of the first dosage of therapeutic agent.

2. The method of claim 1, wherein the tissue layer is a muscular tissue layer.

3. The method of claim 1, wherein the core body is advanced through the patient's skin using a delivery apparatus.

4. The method of claim 1, wherein the first and second therapeutic agent dosages comprise the same therapeutic agent.

5. The method of claim 4, wherein the first and second therapeutic agent dosages comprise different amounts of the therapeutic agent.

6. The method of claim 1, wherein the first and second therapeutic agent dosages comprise a vaccine.

7. The method of claim 1, wherein the first and second therapeutic agent dosages comprise an antibiotic.

8. The method of claim 1, wherein the second time period is substantially longer than the first time period.

9. The method of claim 8, wherein first time period is up to about 20 minutes.

10. The method of claim 8, wherein the second time period is in a range from about one month to about three months.

11. The method of claim 8, wherein the second time period is in a range from about three months to about six months.

12. The method of claim 8, wherein the second time period is in a range from about six months to about twelve months.

13. The method of claim 8, wherein first structure comprises a sugar or maltose.

14. The method of claim 8, wherein the second structure comprises a magnesium alloy.

15. The method of claim 1, wherein the second biodegradable structure is positioned inside the cavity of the first biodegradable structure.

16. The method of claim 1, further comprising a third cavity coupled to the second biodegradable structure, the third cavity being defined by a second shell wall for containing a third dosage of therapeutic agent, the second shell wall having a thickness and material composition selected to time a release of the third dosage to a specified time subsequent to the release of the second dosage, the method further comprising:
    biodegrading the second shell wall in vivo over a third period of time to release the third dosage of therapeutic agent; and releasing the third dosage of therapeutic agent into the tissue of the patient after release of the second dosage of therapeutic agent.

17. The method of claim 16, wherein the first, second and third therapeutic agent dosages comprise the same therapeutic agent.

18. The method of claim 16, wherein a portion of the second shell wall defines a shared wall between the secondary cavity and the third cavity.

* * * * *